United States Patent [19]
Wedel et al.

[11] Patent Number: 5,052,396
[45] Date of Patent: Oct. 1, 1991

[54] NEEDLE GUIDE FOR ULTRASOUND TRANSDUCERS

[75] Inventors: Victor J. Wedel, Rte. 3, Box 121, Washington, Iowa 52353; Rick L. Pruter, Davenport, Iowa

[73] Assignee: Victor J. Wedel, Washington, Iowa

[21] Appl. No.: 433,507

[22] Filed: Nov. 8, 1989

Related U.S. Application Data

[63] Continuation-in-part of Ser. No. 314,291, Feb. 22, 1989, Pat. No. 4,898,178, which is a continuation of Ser. No. 42,387, Apr. 24, 1987, abandoned.

[51] Int. Cl.$^5$ ................................................. A61B 8/00
[52] U.S. Cl. .................................. 128/662.05; 604/116
[58] Field of Search ........... 128/29 A, 660.03, 662.05, 128/759; 604/116

[56] References Cited

U.S. PATENT DOCUMENTS

| 4,489,730 | 12/1984 | Jingu | 128/662.05 |
| 4,497,325 | 2/1985 | Wedel | 604/116 X |
| 4,898,178 | 2/1990 | Wedel | 128/754 X |

FOREIGN PATENT DOCUMENTS

| 2906474 | 8/1979 | Fed. Rep. of Germany | 128/662.05 |

Primary Examiner—Francis Jaworski
Attorney, Agent, or Firm—Gregory G. Williams

[57] ABSTRACT

A disposable needle guide for ultrasound transducers having a means for coupling with a transducer and a multi-slotted, removable insert for receiving and guiding needles of various gauges.

7 Claims, 3 Drawing Sheets

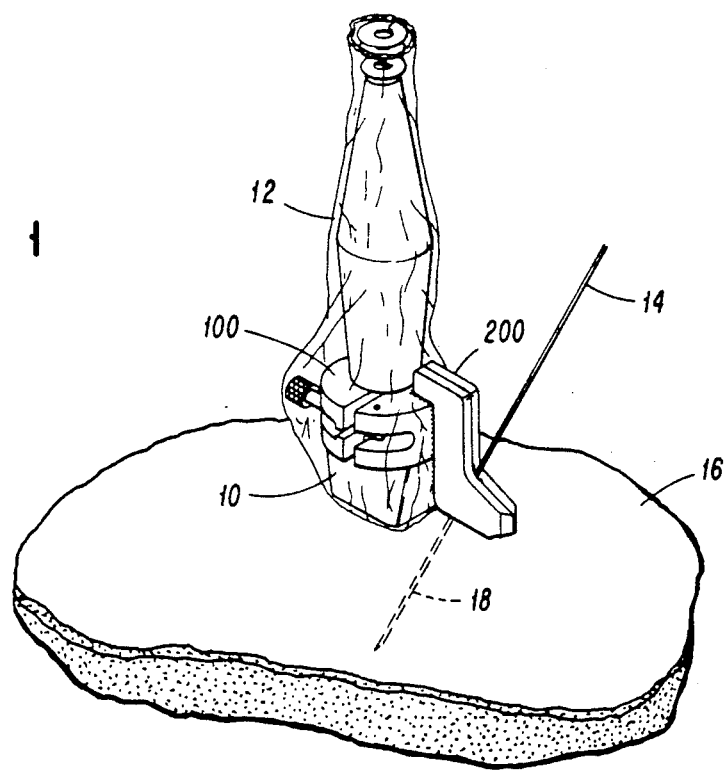
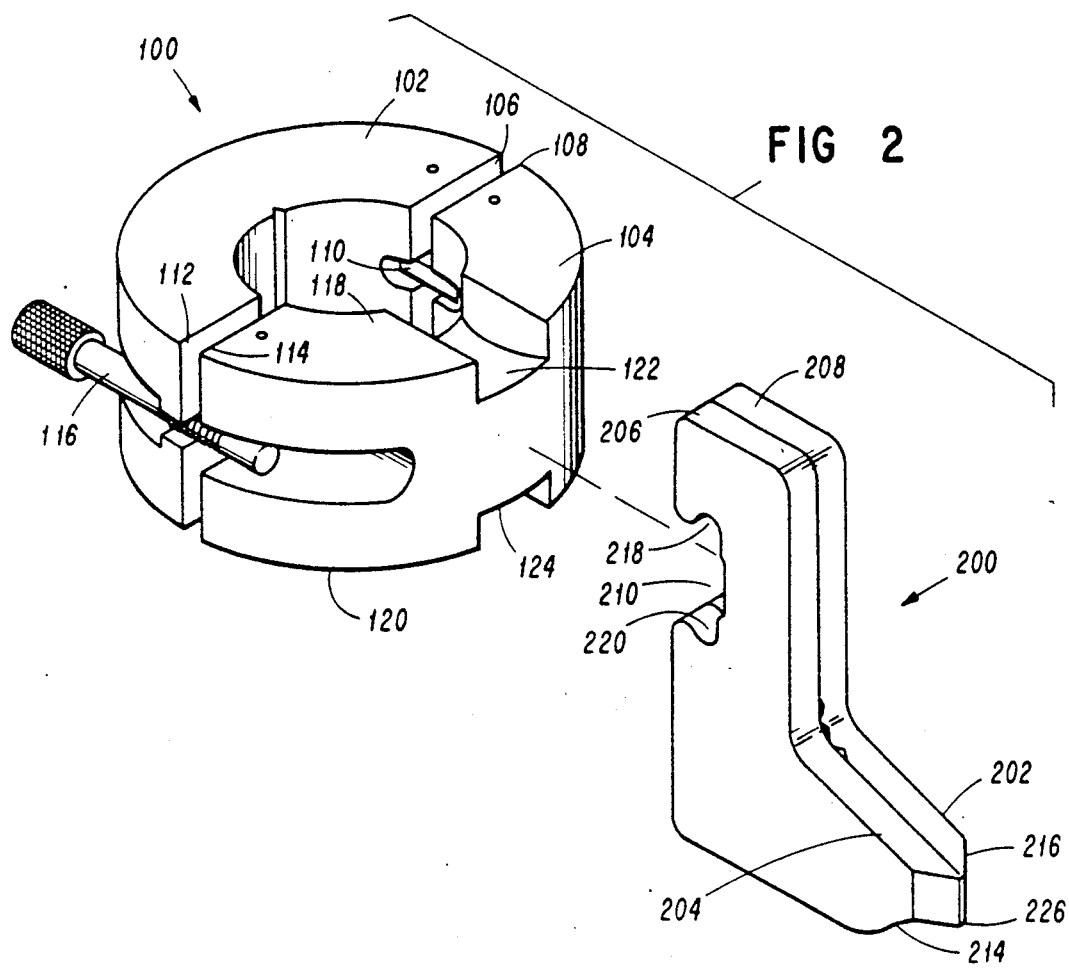

NEEDLE GUIDE FOR ULTRASOUND TRANSDUCERS

CROSS-REFERENCE TO RELATED APPLICATIONS

This is a continuation-in-part application of a co-pending application entitled "Monolithic Disposable Needle Guide for Ultrasound Transducers", having Ser. No. 07/314,291, which was filed by Victor J. Wedel on 02/22/89 now U.S. Pat. No. 4,898,178, which was a continuation of Ser. No. 07/042,387 filed on 04/24/87, (abandoned).

BACKGROUND OF THE INVENTION

This invention relates to the use of ultrasound transducers in conjunction with a needle, biopsy instrument, catheter, etc., in medical procedures. More particularly, it relates to the use of ultrasound transducers and scanners as an aid to physicians, e.g., when obstetricians perform amniocentesis procedures in a sterile clinical atmosphere.

Recently, intense concern has grown among medical and public health professionals relating to the spread of the acquired immune deficiency syndrome, commonly known as AIDS. Fervent debates rage on among top medical researchers about how the AIDS virus can be transmitted, but most scholars agree that one way is through blood to blood exchanges. One such exchange can occur when an unaffected person is the recipient of blood from a donor having AIDS, such as through a transfusion. However, exchange of such a high volume of blood is not necessary for transmission of AIDS to occur. In fact, it is believed that it can be transmitted when a needle which has been exposed to the virus is used by an unaffected person. For this reason, it is commonly believed that drug users who share needles for drug injections are in a high-AIDS-risk category. Similarly, pregnant women undergoing amniocentesis with the aid of ultrasound transducers and their associated needle guides, both of which are used numerously on different women, are at an elevated risk because of the needle's increased exposure to previously used transducers and needle guides.

During some surgical procedures, the health professional may wish to insert two or more successive needles in the patient with each needle having a different diameter or gauge. Often, it is necessary to immediately insert a needle after the removal of another. In such cases, it is desirable to have a needle guide which will accommodate numerous needle sizes.

Consequently, a need exists for an improved needle guide which is capable of rapidly guiding a series of different sized needles in a relatively rapid sequence.

SUMMARY OF THE INVENTION

It is an object of the present invention to provide for an easy removal of needles from the needle guide.

It is a feature of the present invention to include a quick-release tab disposed upon a multi-slotted needle guide insert.

It is an advantage of the present invention to provide a quick-release of the insert by pulling on the tab.

The present invention provides a multi-needle guide for ultrasound transducers which is designed to satisfy the aforementioned need, provide the previously propounded object, include the above described feature, and achieve the earlier articulated advantage.

Accordingly, the present invention includes a multi-slotted needle insert for insertion into a needle guide body, which is attached to an ultrasound transducer.

BRIEF DESCRIPTION OF THE DRAWINGS

FIG. 1 is a perspective and schematic view of a needle guide and mounting bracket of a preferred embodiment of the present invention together with a needle, ultrasound transducer, and associated sterile sheath in a representative environment.

FIG. 2 is an exploded perspective view of a mounting bracket and needle guide of a preferred embodiment of the present invention.

DETAILED DESCRIPTION

Figure 3:
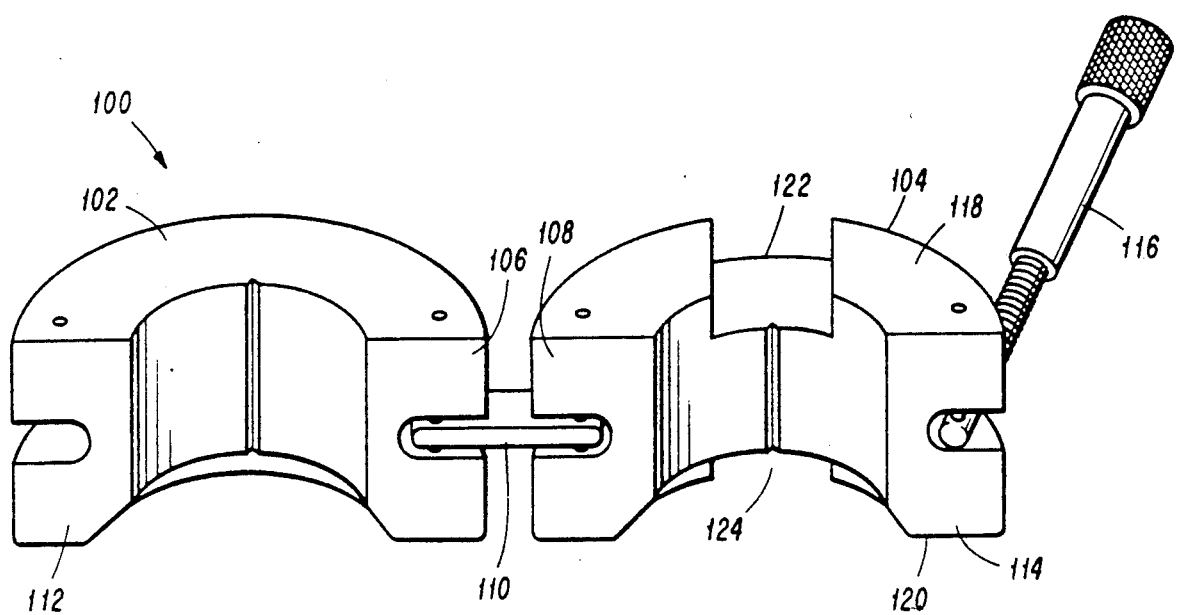
FIG. 3 is a perspective view of a mounting bracket of a preferred embodiment of the present invention in an opened position.

In the following detailed description and drawings, it is understood that like reference numerals refer to like objects throughout.

Now, referring to FIG. 1, there is shown an ultrasound transducer 10, with a mounting bracket, generally designed 100, thereon both of which are disposed within a semitransparent sheath 12. The needle guide, generally designed 200, is shown attached to the bracket 100 with the sheath 12 interposed therebetween, and is further shown having a needle 14 extending therethrough into a representative patient 16. Dashed lines 18 represent the needle 14 under the surface of the skin of the patient 16. The needle 14 may be substituted with a biopsy instrument, catheter, or other medical instrument.

The ultrasound transducer 10, is well known and used in the art, but substitution of an alternative imaging device is contemplated. Similarly, the semi-transparent sheath 12 is well known and is used in the art, but anything, irrespective of its optical characteristics, which serves to isolate the transducer 10 and the bracket 100 from the patient 16, the needle 14, and the needle guide 200, may be substituted.

The configuration of the transducer 10, the needle guide 200, the needle 14, and the patient 16 are such that a physician can firmly grasp the transducer 10 and needle guide with one hand while maintaining contact with the patient 16, and manipulate the needle 14 with the other hand. This maintained physician-to-patient contact is often desired by both doctors and patients alike.

Now referring to FIG. 2, there is shown the mounting bracket 100 together with the needle guide 200. The bracket 100 comprises a first semi-circular and concave member 102 and a second semi-circular and concave member 104. The members 102 and 104 are preferably made of aluminum/lexan plastic. Members 102 and 104 are connected; at a hinge end 106 and 108 respectively, by a hinge 110, and at a latch end 112 and 114 respectively by a latch 116.

Member 104 has a top side 118 and a bottom side 120. A top notch 122 and bottom notch 124 are present in member 104 at its top side 118 and bottom side 120 respectively. Notches 122 and 124 are for receiving guide 200, with the sheath 12 (FIG. 1) interposed therebetween.

Guide 200 has a notched side 202 and a smooth side 204. Sides 202 and 204 have a smooth side top end 206, notched side top end 208, a notched side notch 210, a smooth side bottom end 214 and a notched side bottom end 216.

Notches 210 and 212 are present so that guide 200 may engage with bracket 100 and are formed with recesses 218, 220, 222, and 224 in order to facilitate a quick release.

Sides 202 and 204 are joined together at a common edge 226, to create a hinged link arrangement which enables the sides 202 and 204 to be separated for needle installation and removal.

Now referring to FIG. 3, there is shown the mounting bracket generally designated 100, in an open position.

Figure 4:
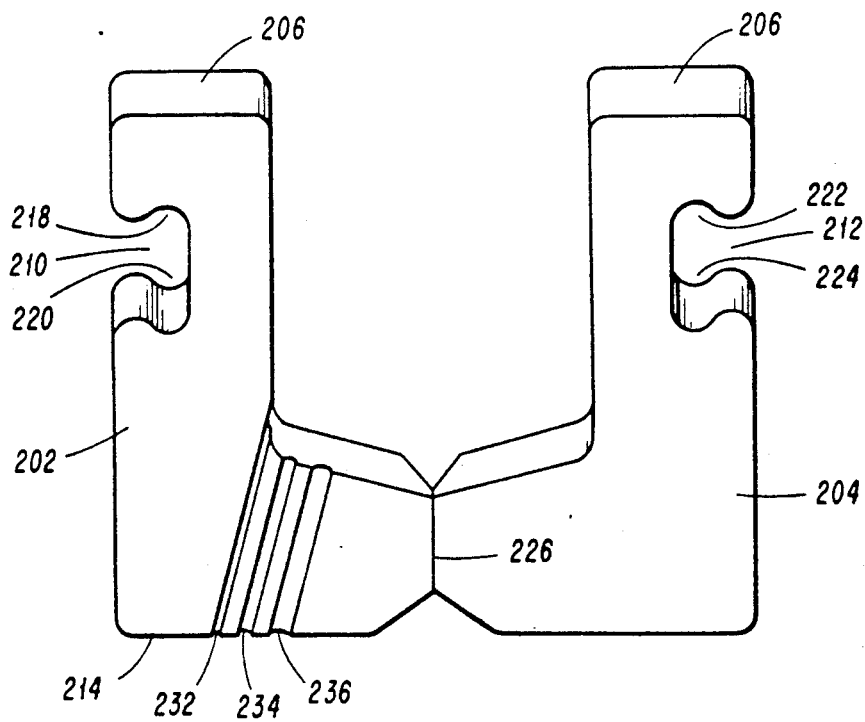
FIG. 4 is a perspective view of a needle guide of a preferred embodiment of the present invention in an opened position.

Now referring to FIG. 4, there is shown the needle guide 200, in an opened position. There is also shown a notched side 202 and a smooth side 204 notched side 202 contain 3 grooves, 232, 234, and 236. Therein for receiving different sized needles.

Figures 5, 6, 7:
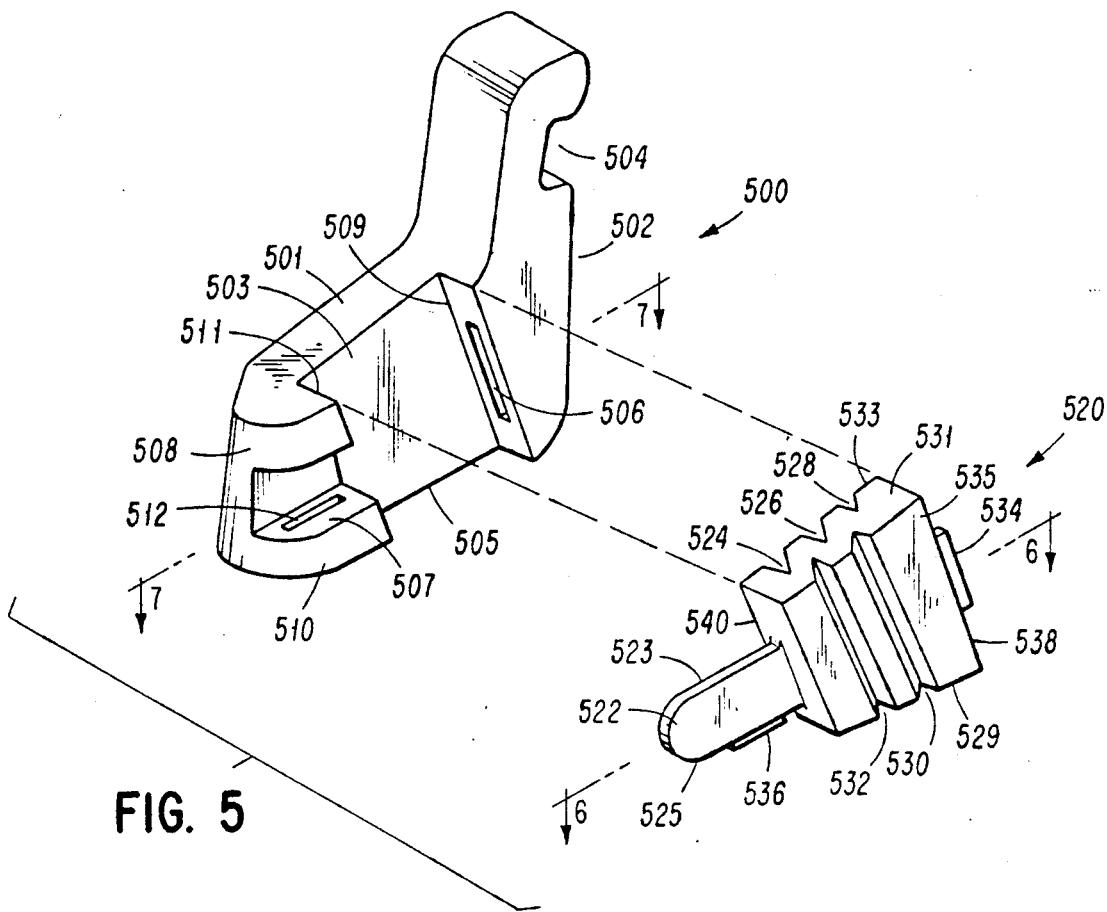
FIG. 5 is an exploded perspective view of a needle guide body and slotted needle insert of a preferred embodiment of the present invention.
FIG. 6 is a cross-sectional view of the needle insert taken on line 6—6 of FIG. 5.
FIG. 7 is a cross-sectional view of the needle guide body taken on line 7—7 of FIG. 5, with the slotted needle insert of FIG. 6, disposed therein.

Now referring to FIG. 5, there is shown a needle guide, generally designated 500. Needle guide body 502 is shown having a notch 504 therein for cooperation with an ultrasound transducer (not shown). Also shown is a top body side 501, a bottom body side 505 and a needle retaining side 503 of body 502. Side 503 has a right side 509 and a left side 511. Preferably, body 502 is constructed of a durable, resilient material, such as plastic. Body 502 having a vertical receiving hole 506 therein, a top receiving member 508, a bottom receiving member 510, having a top horizontal side 507, with a horizontal receiving hole 512 therein. Insert 520 having a quick-release tab 522 thereon having a top tab side 523 and a bottom tab side 525. Insert 520 having a first needle slot 524, a second needle slot 526, a third needle slot 528, a fourth needle slot 530, and a fifth needle slot 532. All of said slots being preferably "V" shaped grooves in insert 520. Insert 520 is shown having a top side 531, a bottom side 529, a first side 533, a second side 535, a tab end 540 and a mating member end 538. Insert 502 having a vertical mating member 534 disposed on mating member end 538 for cooperation with vertical receiving hole 506. Tab 522 has along its bottom tab side 525 a horizontal mating number 536 thereon for cooperating with horizontal receiving hole 512.

Now referring to FIG. 6, there is shown a cross-sectional view of the insert 520 taken on line 6—6 of FIG. 5.

Now referring to FIG. 7, there is shown a cross-sectional view of insert 520 (of FIG. 6) disposed in a cross-sectional view of body 502 taken on line 7—7 of FIG. 5. Vertical mating member 534 is shown disposed within vertical receiving hole 506. Needle slots 524,526 and 528 combine with needle retaining side 503 to form voids for receiving needles (not shown).

It is thought that the needle guide of the present invention, and many of its attendant advantages, will be understood from the foregoing description, and it will be apparent that various changes may be made to the form, construction and arrangement of the parts thereof without departing from the spirit and scope of the invention, or sacrificing all of its material advantages, the form herein before described being merely preferred or exemplary embodiments thereof. It is the intention of the appended claims to cover all such changes.

We claim:

1. A needle guide apparatus comprising:
   a needle guide body having means therein for receiving an ultrasound transducer;
   said needle guide body having a vertical receiving hole therein;
   said needle guide body having a needle retaining side thereon;
   an insert having a vertical mating member thereon for insertion into said vertical receiving hole;
   said insert being detachably disposed adjacent said needle retaining side, so that, a void having an exterior surface is formed with said needle receiving side providing a portion of said exterior surface of said void;
   said insert further having a handle means thereon, said insert being further detachably disposed adjacent said needle retaining side, so that, said insert is detached by pulling said insert away from said needle retaining side, by applying force to said handle means, in a single direction that causes the void to immediately increase in size.

2. A needle guide of claim 1 wherein said needle guide body has a horizontal receiving hole therein.

3. A needle guide of claim 2 wherein said handle means has a horizontal mating member disposed thereon for insertion into said horizontal receiving hole.

4. A needle guide of claim 3 wherein said needle guide body further having a top receiving member thereon and a bottom receiving member thereon.

5. A needle guide of claim 4 wherein said horizontal receiving hole is disposed in said bottom receiving member.

6. A needle guide of claim 5 wherein said handle means is detachably coupled between said top receiving member and said bottom receiving member.

7. A needle guide for use with ultrasound transducers the needle guide comprising in operative combination:
   a needle guide body having a top side, a bottom side and a needle retaining side;
   said needle guide body having a notch therein for receiving an ultrasound transducer;
   said needle guide body having a vertical receiving hole therein disposed between said top side and said bottom side;
   said needle guide body having a top receiving member and a bottom receiving member;
   said bottom receiving member having a horizontal top side with a horizontal receiving hole therein;
   an insert having a top insert side, a bottom insert tab end and a vertical mating member for insertion into said vertical receiving hole, disposed on said mating member end;
   said handle having a horizontal mating member disposed thereon for insertion in said horizontal receiving hole;
   having a plurality of slots therein, with each slot extending from said top insert side to said bottom insert side;

at least one of said plurality of slots being disposed on said first insert side and at least one of said plurality of slots being disposed on said second insert side;

said insert being detachably coupled with said needle guide body, so that said vertical mating member is disposed in said vertical receiving hole and said horizontal mating member is disposed in said vertical receiving hole and said horizontal mating member is disposed in said horizontal receiving hole and said handle being disposed between said top receiving member and said bottom receiving member, so that said needle retaining side is disposed adjacent to said first insert side, so that a void having an exterior surface is formed between said needle guide body and said insert, and said needle retaining side and said at least one of said plurality of slots forming said exterior surface of said void.

* * * * *